CACTACEAE PLANT

Filed Jan. 17, 1974 2 Sheets-Sheet 1

CACTACEAE PLANT

Filed Jan. 17, 1974 2 Sheets-Sheet 2

United States Patent

Plant Pat. 3,693

Patented Mar. 18, 1975

3,693

CACTACEAE PLANT FAMILY

Barnell L. Cobia, Winter Garden, Fla., assignor to B. L. Cobia, Inc., Winter Garden, Fla.

Filed Jan. 17, 1974, Ser. No. 434,025

Int. Cl. A01h *5/00*

U.S. Cl. Plt.—88 1 Claim

ABSTRACT OF THE DISCLOSURE

A new and distinct hybrid plant variety of the Cactaceae family obtained through cross-pollination of a plant of the *Zygocactus truncatus parma* variety with pollen from a *Zygocactus truncatus* variety known commercially as "Christmas Cheer" is principally distinguished from its parents and known related varieties by a growth habit which combines a faster growth rate than its parents, a more upright and compact appearance than its parents, generally broader and thicker cladophylls than its parents, a greater resistance to nutrient deficiencies and fungus diseases than its parents, greater resistance to flower bud abscission than its maternal parent, and a generally larger flower than its maternal parent and which has a bloom life from about 5 to about 8 days, broader tepals than its parents, and perianth tube laminating and forming tepals with generally less recurve tendencies than its parents and with marginal blade areas that in color are dominated by pink, red and/or reddish orange hues.

The invention relates to a new and distinct plant variety of the Cactaceae family and which has been named the *Zygocactus truncatus* Peach Parfait by the inventor.

Certain plants of the Cactaceae family are well known in the foliage plant market and among these are those of the *Zygocactus truncatus* variety commonly known as the "Christmas Cheer" variety. A lesser known variety that has appeared in the foliage plant market is the *Zygocactus truncatus parma* variety. These varieties tend to bloom in the months of November and December in the northern hemisphere.

The variety known as "Christmas Cheer" has a bloom life in the area of about 5 to about 8 days and has a bloom with tepals that are "salmon" colored. The bloom life of the variety provides a suitable shelf life at the retail level of sales but the stems of the variety tend to droop so that the variety lacks the upright appearance considered by many purchasers as evidence of a healthy plant specimen.

The *parma* variety has what may be called a "reddish" colored bloom and has a bloom life of from about 3 to about 6 days. This bloom life provides a somewhat less than satisfactory shelf life at the retail level of sales and the variety suffers from the additional disadvantage that many of the flower buds which start to mature fail to reach maturity. Thus, instead of maturing and forming a bloom, many of the buds drop from the stems and tests have indicated that this bud abscission problem is aggravated when the plant specimens are housed in closed cartons such as are used for shipping purposes in the industry. The *parma* variety also have a low tolerance to nutrient deficiencies and it lacks satisfactory resistance to fungus-type diseases.

A general object of the invention has been to develop a variety of the Cactaceae family which would be somewhat similar colorwise to and competitive with the "Christmas Cheer" variety in the marketplace. Yet another object of the invention has been to develop a variety having the foregoing general objective and which is faster growing and more upright and compact in appearance than the "Christmas Cheer" variety.

The objectives of the invention have been fully realized by the development of the new plant variety hereinafter described in detail. The new plant variety was developed in a nursery located at Winter Garden, Fla., as a hybrid secured by cross-pollinating the flower of a plant of the *Zygocactus truncatus parma* variety with pollen from a plant of the *Zygocactus truncatus* variety commonly known as "Christmas Cheer." The seeds taken from the fertilized seed pod of the *parma* variety were cultivated at the mentioned nursery location and after prolongated observation of the seedlings, the hybridized plant of the new plant variety was selected and asexually reproduced by the inventor at the Winter Garden nursery through the propagation of stem cuttings taken from the original hybrid plant.

Through successive propagations, it has been ascertained that plants of the new plant variety generally resemble the parent varieties but are distinguishable from the parent varieties and from other related varieties known to the inventor by a growth habit which is evident in plants propagated and grown under nursery conditions utilized in the growing of tropical plants at Winter Garden, Fla., as combining the following principal characteristics:

1. A faster growth rate than its parents,
2. A more upright and compact (dense) appearance than its parents, as evidenced by more erect stems with heavier (more frequent) branching,
3. Generally broader and thicker cladophylls than its parents,
4. A hardier growth habit with greater resistance to nutrient deficiencies and fungus diseases than its parents,
5. Greater resistance to flower bud abscission than its maternal parent, and
6. A generally larger flower than its maternal parent and which has (a) a bloom life from about 5 to about 8 days.
(b) broader tepal blades than its parents, and
(c) perianth tube laminating and forming tepals with generally less recurve tendencies than its parents, and with marginal blade areas that in color are dominated by pink, red and/or reddish orange hues.

The accompanying drawings serve, by color photographic means, to illustrate the new plant variety and wherein.

Figure 1:
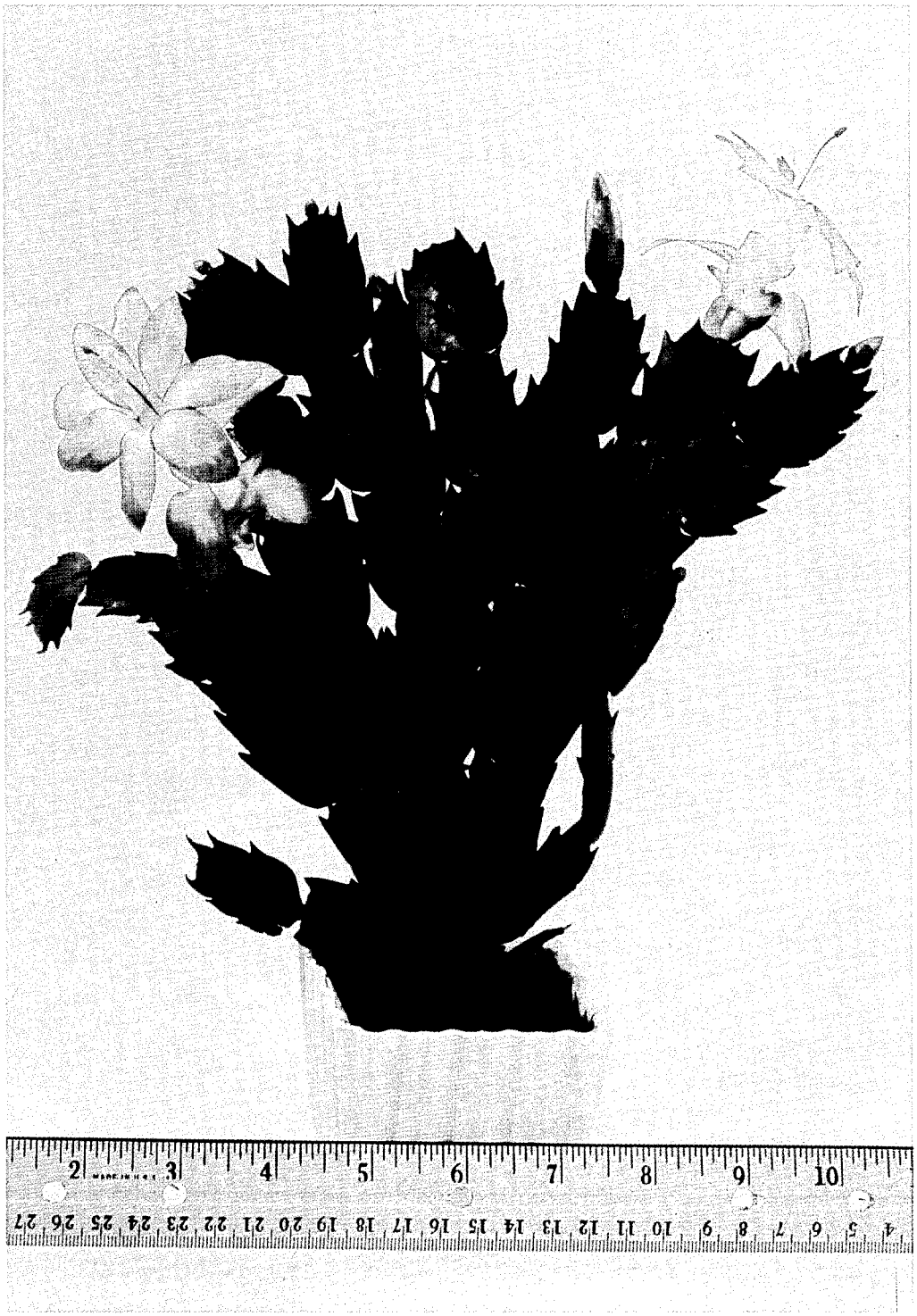
FIG. 1 is a color photograph of a plant specimen of the new plant variety.
Figure 2:
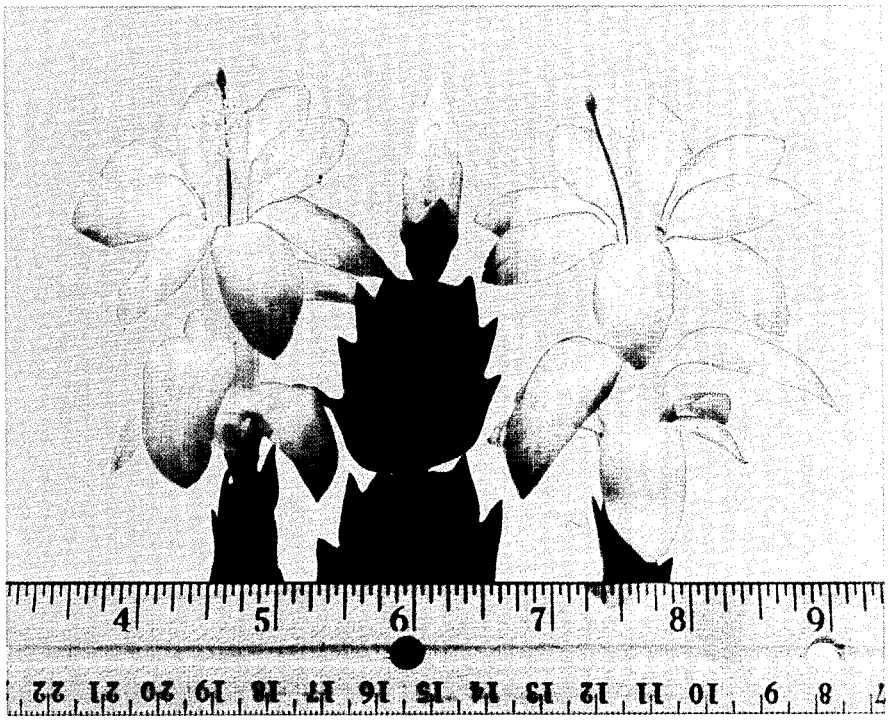
FIG. 2 is a color photograph showing two fully opened blooms of the new plant variety together with a bud of the new variety in an earlier stage of bloom maturity.
Figure 3:
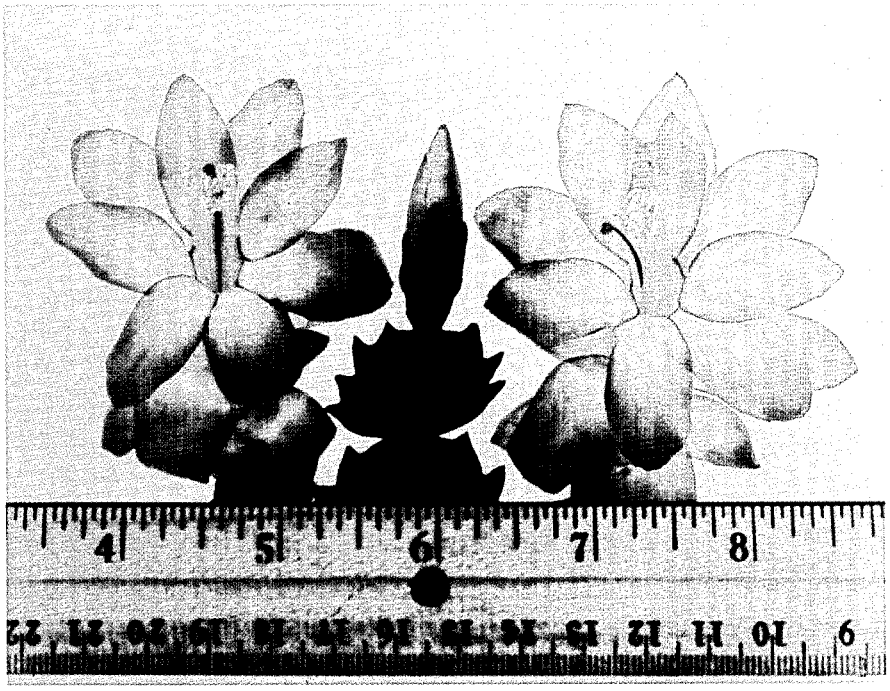
FIG. 3 is another color photograph of the specimens seen in FIG. 2 and which was taken at an angle looking into the throat of the blooms.

The following is a detailed description of the new plant variety with colors and hues, unless otherwise clearly indicated by the text through the absence of color notations, being named in accord with the ISCC–NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plants of less than one year of age from initial propagation and which were grown 50–70% shaded glasshouse nursery conditions in the Winter Garden, Fla., area and wherein temperatures range from 60 to 85° F. during the winter months, from 75 to 95° F. during the summer months and are ambient during intervening periods.

DETAILED PLANT DESCRIPTION

Name: *Zygocactus truncatus* Peach Parfait.

Parentage:

*A. Maternal.*—*Zygocactus truncatus parma.*

*B. Paternal.*—*Zygocactus truncatus* variety known commercially as "Christmas Cheer."

Classification:

*A. Botanic (Britton and Rose, The Cactaceae, Constable and Co., Ltd., London, 1937, Vol. IV).*—(1) Family: Cactaceae. (2) Tribe: Cereeae. (3) Sub-tribe: Epiphyllanae. (4) Genus: Zygocactus. (5) Species: *truncatus* (Haworth) Schumann.

*B. Commercial.*—Thanksgiving-Christmas blooming cactus.

Form: Terrestrial, shade-loving, succulent, leafless plant with jointed and branched stems.

Stems:

*A. General.*—Irregular with usually multi-chotomous branching of both upright and pendulous, adventitiously rootable, flattened cladophylls that have a prominent midrib and prominently toothed lateral wings.

*B. Cladophylls.*—(1) General: Elongated and flat with transversely elongated, areole bearing, truncated apex, with inwardly tapering basal wing margins that merge through a broad usually pointed basal juncture with the cladophyll therebelow, and with an axillary areole associated with each tooth. (2) Midrib: (a) General—Extends longitudinally of cladophyll and continuously through joints with laterally tapering cortex at wing insertions. Pith surrounding vascular bundles that branch and provide lateral extensions of the vascular system to marginal teeth. (b) Texture—Smooth waxy epidermis with wax in small embedded scales and becoming corky in basal stem areas with age. (c) Size (2–6 mos. old)—(1) Length—Usually between 39 and 52 mm. with the average for respective plant specimens being usually between 44 and 48 mm. (2) Thickness—Usually between 2.3 and 5.1 mm. with the average for respective plant specimens being usually between 3.2 and 3.6 mm. (d) Color (at maturity)—Commonly moderate yellow green (near 5 GY 5/6) (5 GY 6/6) (2.5 GY 5/6). (3) Wings: (a) General shape—Generally flattened from midrib cortex to tooth insertions with slight thinning taper toward margins. (b) Margins—Toothed (modified leaves). (c) Texture—Succulent to leathery with smooth waxy epidermis having wax arranged in small embedded scales and becoming corky in basal plant areas with age. (d) Size (2–6 mos. old)—(1) Center thickness—Usually between 1.4 and 3.1 mm. (2) Width (as measured from cladophyll axis to most offset lateral areole)—Usually between 10 and 18 mm. (e) Color (at maturity)—Commonly moderate olive green (7.5 GY 3/4) (7.5 GY 4/4) (near 7.5 GY 4/6) and/or dark yellowish green (10 GY 4/4) (near 10 GY 3/4). (4) Teeth: (a) General shape—Generally flattened and tapered along margins from wing insertions to an apex having a hyaline, single cell, pointed spine with nonpredictable bending. (1) Adaxial marginal shape—Usually straight to slightly convex. (2) Abaxial marginal shape—Somewhat irregular with tendencies toward a medial indentation that provides—(a) a distal terminus for a convex proximal marginal edge portion, and (b) a basal terminus for a distal marginal edge portion that varies from straight to convex. (b) Orientation—Usually projects generally distally of cladophyll base in an alternate arrangement and with the median of the tooth angles (as measured at the distal side of the intersect with the cladophyll axis of a line through the tooth apex and the midpoint between the abaxial and adaxial areoles thereof) formed by the non-basal teeth of a cladophyll usually being between 10° and 26°. (c) Margins—Entire. (d) Texture—Succulent to leathery with smooth waxy epidermis having wax in small embedded scales and becoming corky in basal plant areas with age. (e) Number—Usually from 6 to 8 per cladophyll. (f) Size (2–6 mos. old)—(1) Center thicknesses—Usually between 0.7 and 1.8 mm. (2) Areole to apex dimension (adaxial marginal side)—Usually between 2 and 7 mm. for teeth located distally of basal teeth. (g) Color (at maturity)—Commonly moderate olive green (7.5 GY 3/4) (7.5 GY 4/4) (near 7.5 GY 4/6) and/or dark yellowish green (10 GY 4/4) (near 10 GY 3/4). (5) Areoles: (a) Terminal areole—Large elongated oval-shaped with several acicular bristles, copious multi-cellular hairs, and several buds that may mature into either new cladophylls or flowers. The opposite ends of the areole are located adjacent to subsidiary areoles which are in turn located at the axils of teeth that are located at the distal end of cladophyll. (b) Axillary areoles—Acicular bristles without glochidia but having copious, short, brownish to colorless, multicellular hairs. In areoles that are located below the teeth at the distal end of the cladophyll, there is usually only one bud that is frequently latent.

Buds: Unarmored, ovoid and chlorophyllous.

Flowers:

*A. General.*—Sessile, zygomorphic, usually solitary, terminal, perfect and epigynous with double hypanthium and tepals (undifferentiated whorled sepals and petals) having a spiral emergence as a perianth provided with a sepaloid series of free tepals, a tube laminating series of tepals, and a tube forming series of united tepals.

*B. Sepaloid series.*—(1) General: Free tepals inserted on top of ovary. (2) Shape: Tapered from insertion to apex in outer members of whorl and grading inwardly in the whorl to provide progressively broader apices and longer base-tip dimensions. All members have pointed tip and entire margins with sparse irregular teeth appearing mainly in apex areas of the inner members of the whorl. (3) Texture: Succulent and glabrous outer whorl members and grading inwardly in the whorl to silken blades with fleshy basal areas. (4) Number: Usually from 8 to 10. (5) Size (at full bloom): (a) Base-tip dimension—Usually less than 28 mm. (b) Maximum width dimension—Usually less than 15 mm. (6) Color: Varies from the smallest to the largest tepals in outer whorl members with the smallest tepal usually having a continuous field that in color has a yellow green hue while the largest tepal usually has a marginal blade area which in color is dominated by pink, red, yellowish pink and/or reddish orange hues and a basal area which in color is dominated by a yellow green hue, the colors in the marginal and basal areas tending to surround and merge inwardly with a translucent white center field. Commonly moderate yellow green (5 GY 7/6) and/or strong yellow green (5 GY 6/8) in the continuous fields and basal areas and deep pink (2.5 R 6/10) (2.5 R 6/8) (5 R 6/10), moderate red (near 2.5 R 5/10) (near 5 R 5/10) (2.5 R 5/8) (2.5 R 4/8) (5 R 4/10), strong yellowish pink (near 7.5 R 7/8) and/or moderate reddish orange (near 7.5 R 6/8 in marginal areas. The inner whorl members having a translucent white basal area that extends distally in the tepal and merges with a marginal blade area which in color is dominated by reddish orange, pink, yellowish pink and/or red hues. The translucent white basal areas commonly have a greenish cast at the tepal insertion and there is some tendency for the cast to extend distally of the insertion along the tepal axis. Commonly moderate reddish orange (7.5 R 6/10), deep pink (5 R 6/10) (near 2.5 R 6/10), strong pink (2.5 R 7/8), strong yellowish pink (5 R 7/8) and/or moderate red (5 5/8) (2.5 R 5/8) (2.5 R 5/10). (7) Orientation at full bloom: Varying inwardly in the whorl from erect to recurve.

*C. Tube laminating series.*—(1) General: Tepals inserted on ovary and basally united below the throat as outer laminations on the perianth tube and with progressively greater amounts of basal fusion inwardly in the whorl. (2) Shape: Grading inwardly in whorl with progressively longer base-tip dimensions and with ovate blades broadening inwardly in the whorl, and having acute tips. Entire margins with sparse irregular teeth mainly in apex areas. (3) Texture: Succulent, slightly fleshy, basal areas with silken blades. (4) Number: Usually 4 or 5. (5) Size (at full bloom): (a) Base-tip dimensions—Usually between 32 and 51 mm. (b) Maximum width dimensions—Usually between 12 and 20 mm. (6) Color: Tepals with translucent white basal areas that extend distally in the tepal and merge with marginal blade areas that in color are dominated by pink, red and/or reddish orange hues. Commonly deep pink (5 R 6/10), strong red (5 R 5/12), moderate red (5 R 5/8) (2.5 R 5/10), moderate reddish orange (7.5 R 6/10) (7.5 R 5/10) (7.5 R 5/8) and/or strong reddish orange (7.5 R 5/12) in marginal blade areas. (7) Orientation at full bloom: Perpendicular to recurved.

*D. Tube forming series.*—(1) General: Tepals basally united to form hollow perianth tube that is inserted on ovary and equipped with irregular carina keel) at throat. (2) Shape: (a) Perianth tube—Elongated and ellipsoidal in cross section with major ellipsoidal axis arranged generally perpendicular to the general plane of the supporting cladophyll. (b) Blades—Nearly zygomorphic and elliptic with acute tip. Entire margins with sparse, irregular teeth mainly in apex area. (c) Carina (keel)—Transcending with regular scalloped pattern having troughs located at respective tepals axes. (3) Texture: (a) Perianth tube—Thick, succulent and slightly ribbed. (b) Blades—Translucent and silken. (c) Carina (keel)—Fleshy. (4) Blade number: Usually 8. (5) Size (at full bloom): (a) Perianth tube— (1) Base to keel length—Usually between 30 and 38 mm. along axis of tube with average lengths difference between measurements along dorsal and ventral sides for respective spectimens usually being between 2.5 mm. and 6.0 mm. (2) Internal major axis (at throat)—Usually between 7 and 13 mm. when measured perpendicular to axis of perianth tube. (3) Internal minor axis (at throat)—Usually between 7 and 9 mm. when measured perpendicular to axis of perianth tube. (b) Blades— (1) Length (keel to tip)—Usually between 30 and 34 mm. (2) Width (maximum)—Usually between 13 and 17 mm. (6) Color (at full bloom): (a) Perianth tube—Translucent white basal area that merges with a distal area which in color has a purplish pink hue. Commonly moderate purplish pink (2.5 RP 7/6) (5 RP 7/6) (7.5 RP 7/6), light purplish pink (5 RP 8/6) and/or pale purplish pink (2.5 RP 8/4) (7.5 RP 8/4) in distal areas. (b) Blades—Tepal blades with marginal blade areas which in color are dominated by reddish orange, red and/or pink hues that merge with a translucent white basal blade area located distally of the keel. Commonly moderate reddish orange (near 7.5 R 6/10), strong reddish orange (7.5 R 5/12), moderate red (near 5 R 5/10), strong red (near 5 R 5/12) and/or deep pink (near 5 R 6/10). (c) Carina (keel)—Commonly strong reddish purple (10 P 5/10) (2.5 RP 5/10) (10 P 4/10) (10 P 4/8), moderate reddish purple (2.5 RP 5/8) (2.5 RP 5/6) and/or moderate purplish red (5 RP 5/10) (near 5 RP 4/8) (7.5 RP 4/8). (7) Orientation at full bloom: Acute to recurve.

*E. Androecium (stamens).*— (1) General: Numerous exserted and diadelpholus stamens with one group having filaments basaly fused to the perianth tube and the other group having filaments basally united to form a nectary housing, thin annulus around the style and which is provided with a thin, deflexed, irregularly toothed margin or ruffle at the throat of the annulus. (2) Stamen number: (a) Tube attached group—Usually between 64 and 76. (b) Basally united group—Usually between 15 and 19. (3) Filament: (a) General—Translucent and glabrous with another connective. (b) Shape—Long, slender and gradually tapering from base to anther connective. (c) Texture—Glabrous and silken. (d) Color—A translucent white. (e) Size (at full bloom)—(1) Length—(a) Tube attached group—Usually between 38 and 47 mm. (b) Basally united group—Usually between 42 and 48 mm. (2) Diameter—Usually between 0.25 and 0.3 mm. intermediate the opposite ends. (4) Anthers: (a) General—Adnate with four longitudinally dehiscent pollen sacs. (b) Shape—Elongated. (c) Texture—Waxy. (d) Color (prior to dehiscing)—Usually pale yellow (5 Y 9/4) and/or pale yellowish green (7.5 Y 9/4). (e) Size (immediately prior to dehiscing)—Usually between 1.2 and 2.3 mm. in length. (f) Sterility—Very fertile.

*F. Gynoecium (pistil).*—(1) General: Compound, parietal placentation with united style surrounded by annular diffuse nectary at its insertion. (2) Style: (a) General—Hollow, stout and inserted in ovary. (b) Shape—Elongated, cylindrical and generally tapering. (c) Texture—Fleshy and glabrous with short inner glutinous hairs at distal end. (d) Color—Commonly moderate purplish red (near 10 RP 5/10) (near 10 RP 4/10), moderate red (near 2.5 R 5/10) (near 2.5 R 4/10) (near 5 R 4/10), strong red (5 R 4/12), vivid red (near 5 R 4/4) and/or deep reddish orange (near 7.5 R 4/12). (e) Size (at full bloom)— (1) Length—Usually between 60 and 66 mm. (2) Diameter—Usually between 0.7 and 1.0 mm. intermediate the opposite ends. (3) Stigma: (a) General—Exserted and erect with usually from 4 to 6 inner marginally adhering lobes that are commonly bifurcated. (b) Shape—Elongated and tapering toward lobe tips and having relatively blunt apices. (c) Texture—Fleshy and smooth with short glutinous hairs. (d) Color—Commonly moderate purplish red (5 RP 5/10), and/or strong reddish purple (2.5 RP 5/10) (near 2.5 RP 4/10) (near 10 P 5/10). (e) Size (lobe length at full bloom)—Usually between 3.5 and 5.0 mm. along inner margins. (4) Ovary: (a) General—Epigynous with thin epidermis and distally located concavity and with single cavity having 5 or 6 carpels with numerous ovules. (b) Shape—Terete to ovoid and generally broadening from insertion to floral end. (c) Texture—Succulent and glabrous with thin outer epidermis. (d) Color—Commonly moderate yellow green (2.5 GY 7/6) (near 2.5 GY 6/6) (5 GY 7/4) (near 5 GY 7/6) (near 5 GY 6/6). (e) Size (at full bloom)— (1) Length (insertion to concavity base)— Usually between 7 and 8.5 mm. (2) Major axis (distal end of concavity)—Usually between 7.5 and 9.5 mm. (3) Minor axis (distal end of concavity)— Usually between 6.5 and 8.8 mm. (f) Sterility factor—Very fertile.

Growing characteristics: A faster growth rate under comparable growing conditions than either parent, a more upright and compact (denser) appearance than its parents, as evidenced by more erect stems with heavier (more frequent) branching, a greater resistance than its parents to nutrient deficiencies and to fungus-type diseases, a bloom life (from initial tepal separation to initial tepal withering) of from about 5 to about 8 days and substantially less flower bud abscission than its maternal parent.

The following is a general description of a specimen of the new plant variety that was grown from the propagation of a single cladophyll in a nursery at Winter Garden, Fla.

Age of plant: 7 months from initial propagation.
Branches from propagated cutting: 3.
Total number of cladophylls grown from cutting: 25.

General:

| Branch No. | No. of cladophylls | Max. length, mm. | No. of tips |
|---|---|---|---|
| 1 | 8 | 228 | 2 |
| 2 | 8 | 153 | 4 |
| 3 | 9 | 180 | 4 |

Midribs:

| Branch No. | Length (avg.), mm. | Thickness (avg.), mm. |
|---|---|---|
| 1 | 47 | 4.1 |
| 2 | 44 | 3.7 |
| 3 | 41 | 3.2 |

Wngs:

| Branch No. | Center thickness (avg.), mm. | Max. width (avg.), mm. |
|---|---|---|
| 1 | 2.81 | 17 |
| 2 | 1.97 | 14 |
| 3 | 2.47 | 14.1 |

Teeth:

| Branch No. | No./cladophylls (avg.) | Center thickness (avg.), mm. | Areole to apex dimension (avg.), mm. | Tooth angle (median), degrees |
|---|---|---|---|---|
| 1 | 7.5 | 1.45 | 4.95 | 15 |
| 2 | 6.7 | 1.25 | 4.3 | 20 |
| 3 | 7.3 | 1.14 | 4.7 | 23 |

Cladophyll color: Moderate olive green (7.5 GY 3/4) (7.5 GY 4/4), dark yellowish green (10 GY 4/4) (10 GY 3/4).

The following is a general description of a flower of the new plant variety which bloomed in November on a plant grown under shaded glasshouse nursery conditions in Winter Garden, Fla.

Bloom life: 7 days.
Sepaloid series of tepals:

(*1*) *Number.*—8.

(*2*) *Size* (*at full bloom*).—(a) Maximum base-tip dimension—25 mm. (b) Minimum base-tip dimension—4 mm. (c) Maximum width dimension—14 mm.

(*3*) *Color.*—Moderate yellow green (5 GY 7/6) in continuous field of smaller tepals and in basal area of largest tepal in outer whorl. Deep pink 2.5 R 6/8), moderate red (near 2.5 R 5/10) (2.5 R 5/8) and moderate reddish orange (near 7.5 R 6/8) in marginal areas of largest tepal of outer whorl members. Deep pink (5 R 6/10), strong pink (2.5 R 7/8) and moderate red (2.5 R 5/8) (5 R 5/8) in marginal areas and a translucent white in basal areas of inner whorl members.

Tube laminating series:

(*1*) Number.—4.

(*2*) *Size* (*at full bloom*).—(a) Maximum base-tip dimension—50 mm. (b) Minimum base-tip dimension—31 mm. (c) Maximum width dimension—18 mm. (d) Minimum width dimension—12 mm.

(*3*) *Color.*—Deep pink (5 R 6/10), moderate red 2.5 R 5/10) (5 R 5/8), moderate reddish orange (7.5 R 5/8) in marginal blade areas and translucent white in basal areas.

Tube forming series of tepals:

(*1*) *Number.*—8.

(*2*) *Size* (*at full bloom*).—(a) Perianth tube—(1) Base to keel length—34 mm. (2) Interior major axis (at throat)—11 mm. (3) Interior minor axis (at throat)—8 mm. (b) Blades—(1) Maximum length (keel to tip)—33 mm. (2) Minimum length (keel to tip)—32 mm. (3) Maximum width—16 mm. (4) Minimum width—14 mm.

(*3*) *Color.*—(a) Perianth tube—A translucent white basal area and pale purplish pink (2.5 RP 8/4), light purplish pink (5 RP 8/6) in distal area. (b) Blades—Deep pink (near 5 R 6/10), strong red (near 5 R 5/12), moderate reddish orange (near 7.5 R 6/10) and strong reddish orange (7.5 R 5/12) in marginal blade areas with translucent white area adjacent keel on upper epidermis. (c) Carina (keel)—Moderate reddish purple (2.5 RP 5/8), moderate purplish red (5 RP 5/10).

Androecium:

(*1*) *Stamen number.*—(a) Tube attached group—72. (b) Basally united group—18.

(*2*) *Filaments.*—(a) Color—A translucent white. (b) Size (at full bloom)—(1) Length—(a) Tube attached group—45 mm. (avg.). (b) Basally united group—44 mm. (avg.). (2) Diameter—About 0.30 mm. intermediate the opposite ends.

(*3*) *Anthers.*—(a) Color (before dehiscing)—Pale yellowish green (7.5 Y 9/4). (b) Size—1.7 mm. (avg.). (c) Sterility—Very fertile.

Gynoecium (pistil):

(*1*) *Style.*—(a) Color—Strong red (5 R 4/12), deep reddish orange (near 7.5 R 4/12). (b) Size (at full bloom)—(1) Length—63 mm. (2) Diameter—About 0.9 mm. intermediate the opposite ends.

(*2*) *Stigma.*—(a) Color—Moderate purplish red (5 RP 5/10), strong reddish purple (2.5 RP 5/10) (near 10 P 5/10). (b) Size (lobe length)—About 4.2 mm.

(*3*) Ovary.—(a) Color—Moderate yellow green (near 5 GY 7/6) (2.5 GY 7/6). (b) Size (at full bloom)—(1) Length (insertion to concavity base)—8.0 mm. (2) Major axis (distal end of concavity)—8.9 mm. (3) Minor axis (distal end of concavity)—7.8 mm. (c) Sterility—Very fertile.

I claim:

1. The new and distinct hybrid plant variety of the Cactaceae family as described and illustrated and which is primarily distinguished by growth habit that combines the following characteristics:

1. A faster growth rate than its parents.
2. A more upright and compact appearance than its parents,
3. Generally broader and thicker cladophylls than its parents,
4. A hardier growth habit with greater resistance to nutrient deficiences and fungus diseases than its parents,
5. Greater resistance to flower bud abscission than its maternal parent, and
6. A generally larger flower than its maternal parent and which has (a) a blom life from about 5 to about 8 days,
(b) broader tepal blades than its parents, and
(c) perianth tube laminating and forming tepals with generally less recurve tendencies than its parents, and with marginal blade areas that in color are dominated by pink, red and/or reddish orange hues.

References Cited

UNITED STATES PATENTS

P.P. 3,574 6/1974 Cobia ---------- Plants—88

ROBERT E. BAGWILL, Primary Examiner

PO-1050
(5/69)

UNITED STATES PATENT OFFICE
CERTIFICATE OF CORRECTION

Patent No. P.P. 3693 Dated March 18, 1975

Inventor(s) Barnell L. Cobia

It is certified that error appears in the above-identified patent and that said Letters Patent are hereby corrected as shown below:

Column 5, Line 7 (5 5/8) should read -- (5 R 5/8) --;
Line 53 "spectimens" should read -- specimens --;
Column 6, Line 19 "another" should read -- anther --;
Column 9, Line 1 "blom" should read -- bloom --.

Signed and Sealed this
seventh Day of October 1975

[SEAL]

Attest:

RUTH C. MASON
*Attesting Officer*

C. MARSHALL DANN
*Commissioner of Patents and Trademarks*